United States Patent [19]

Brown

[11] Patent Number: 5,002,013
[45] Date of Patent: Mar. 26, 1991

[54] BUTTERFLY HIBERNATION CONTAINER

[76] Inventor: Arthur C. Brown, P.O. Box 277, West Kingston, R.I. 02892

[21] Appl. No.: 436,075

[22] Filed: Nov. 16, 1989

[51] Int. Cl.$^5$ ............................................... A01K 1/00
[52] U.S. Cl. ...................................... 119/15; 119/174
[58] Field of Search ................... 119/1, 6, 15, 23, 52.2, 119/57.8

[56] References Cited

U.S. PATENT DOCUMENTS

| | | | |
|---|---|---|---|
| 2,900,955 | 8/1959 | Danielsen | 119/15 |
| 3,509,855 | 5/1970 | Priddy, Jr. | 119/15 |
| 3,611,994 | 10/1971 | Bailey et al. | 119/15 X |
| 4,167,917 | 9/1979 | Noll | 119/23 |
| 4,442,793 | 4/1984 | Overpeck et al. | 119/23 |

Primary Examiner—Gene Mancene
Assistant Examiner—T. Price
Attorney, Agent, or Firm—Barlow & Barlow, Ltd.

[57] ABSTRACT

A butterfly hibernation container is formed of six adjoining walls and is provided in the interior thereof with tree bark placed in the container to resemble a wood pile which forms natural interior crevices. An exterior crevice is provided by spacing a plaque from one of the walls to create a crevice, all crevices being familiar habitat for butterflies.

1 Claim, 1 Drawing Sheet

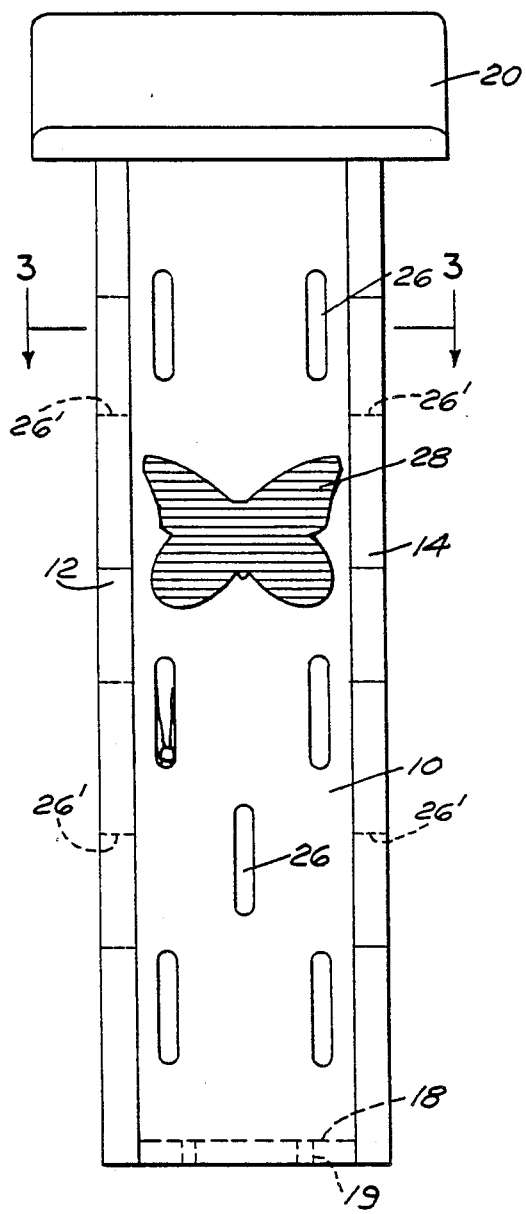
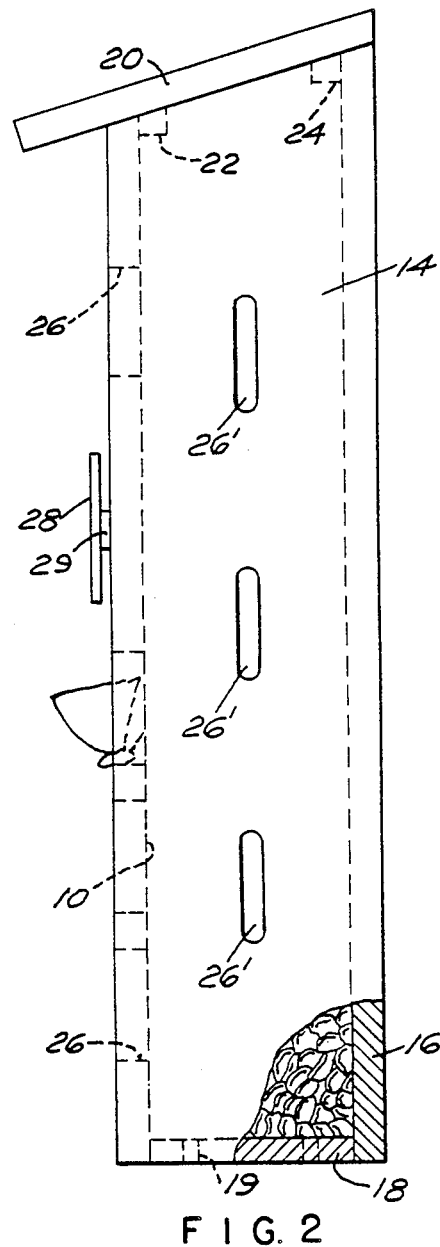
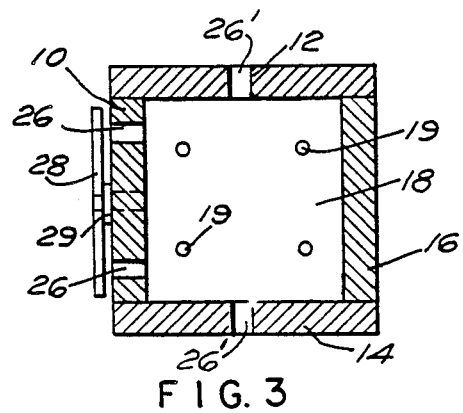
FIG. 1
FIG. 2
FIG. 3

BUTTERFLY HIBERNATION CONTAINER

BACKGROUND AND SUMMARY OF THE INVENTION

There are at least ten species of butterflies that hibernate in trees, as for example in crevices behind the bark. They may also hibernate in holes, in woodpiles, in eaves of houses or even behind a shutter of a house or anywhere they can find a crevice. It is apparently becoming more difficult for some butterflies to find a site to hibernate and accordingly, there is a need, particularly for individuals who wish to attract butterflies near flowers, to provide a hibernation place for the butterflies.

The invention, therefore, contemplates the utilization of a box or a container which will have four vertical walls of considerable height, preferably with a removable roof and a bottom wall which will be provided with suitable drainage. One of the vertical walls of the container will be provided with a plurality of vertical slots of a sufficient size to permit a butterfly to enter. Within the container there will be provided a plurality of crevices within bark that may be loosely placed therein and a further crevice is provided by placing a decorative plaque a small distance away from one outside wall.

DESCRIPTION OF THE DRAWING

FIG. 1 is a front elevational view of the butterfly hibernation container constructed in accordance with my invention;

FIG. 2 is a side elevational view thereof; and

FIG. 3 is a sectional view taken on lines 3—3 of FIG. 1 with the bark removed for clarity.

DESCRIPTION OF THE PREFERRED EMBODIMENT

With reference to the drawing, there is illustrated a container having a front wall 10, a pair of side walls 12 and 14 and a rear wall 16. There is also provided a bottom wall 18 and a with a plurality of drainage holes 19, while a roof 20 is loosely held in place by cleats 22, 24, for example, or by any other suitable means and may even be hinged to the back wall. The front wall 10 is provided with a plurality of entrance slots 26 and the side walls 12 and 14 are also provided with slots 26'. For decorative purposes, there is provided a plate or plaque 28 that is spaced from the front wall by a spacer 29. The plate is illustrated in the form of a butterfly which may be suitably colored. The drawing is shaded for the color blue, in as much as blue is the most effective color to attract butterflies. The fact that the plate 28 is raised from the front wall provides at least some area in the form of a crevice which some butterflies may desire to use as a hibernation place.

By referring now to FIG. 2, it is seen that within the container the interior of the box is filled partway with tree bark which would simulate a wood pile to a butterfly which will crawl through the entrance slot 26 and into the crevices created between the individual pieces of bark for hibernation. As noted above, the roof 20 is made removable which will permit the insertion of tree bark and this will also allow one to count hibernating butterflies Essentially, as mentioned before, the butterflies that hibernate, at least in the United States, are known to be the Morning Cloak, the Compton Tortoise Shell, Milbert's Tortoise Shell, California Tortoise Shell, Hoary Comma (Zephyr), Question Mark, Angel Wing Satyr, Green Comma, Gray Comma and Red Admiral. These different species are known to hibernate at different times of the year and by utilizing a hibernation box such as is disclosed herein, one can attract butterflies to be near flowers. It is also known that it would be helpful to attract butterflies to the container by utilizing for example, a blue nylon scouring pad that has high energy fruit sugar in it or on it. This may be secured to the outer walls and as mentioned above, blue is the primary color to which butterflies are attracted for this group of species so it is important to use this shade of color. The high energy sugar, such as fructose, would be a food for the butterfly.

It is desirable that the hibernation box be made from a clear, rough sawn western red cedar which will provide a surface for butterflies to cling to. Western red cedar is the preferred material as it has a natural chemical which is distasteful to many insects that damage wood, so a box of this material is one that will be long lasting.

I claim:

1. A butterfly hibernation container comprising a six walled container having two elongated side walls, an elongated front, an elongated back, and a bottom wall all secured together, a removable roof, the interior of the container being loosely filled with tree bark to form crevices within the container, a wooden plate spaced from and parallel to the outside of at least one of the elongated walls of the container a small distance to provide a crevice and a plurality of elongated slots in the front and side walls communicating with the interior.

* * * * *